(12) United States Patent
Dafni

(10) Patent No.: US 6,400,789 B1
(45) Date of Patent: Jun. 4, 2002

(54) ON-LINE IMAGE RECONSTRUCTION IN HELICAL CT SCANNERS

(75) Inventor: Ehud Dafni, Caesarea (IL)

(73) Assignee: Philips Medical Systems Technologies Ltd., Haifa (IL)

(*) Notice: Subject to any disclaimer, the term of this patent is extended or adjusted under 35 U.S.C. 154(b) by 0 days.

(21) Appl. No.: 09/367,769

(22) PCT Filed: Feb. 12, 1998

(86) PCT No.: PCT/IL99/00075

§ 371 (c)(1),
(2), (4) Date: Jan. 19, 2000

(87) PCT Pub. No.: WO98/36691

PCT Pub. Date: Aug. 27, 1998

(30) Foreign Application Priority Data

Feb. 20, 1997 (IL) ................................................ 120277
Feb. 20, 1997 (IL) ................................................ 120278

(51) Int. Cl.[7] ................................................ A61B 6/00
(52) U.S. Cl. ................ 378/15; 378/20; 378/4
(58) Field of Search ................ 378/15, 8, 20, 378/901; 250/491.1

(56) References Cited

U.S. PATENT DOCUMENTS 5,485,493 A   1/1996  Heuscher et al.
5,524,130 A   6/1996  Ohhashi
5,566,220 A * 10/1996 Saito et al. .................. 378/138
5,878,103 A *  3/1999 Sauer et al. ................... 378/15
6,118,839 A *  9/2000 Dafni et al. .................... 378/15

FOREIGN PATENT DOCUMENTS

EP    0 655 713 A    5/1995
FR    2 679 435 A    1/1993
WO    WO 98/36689    2/1997

* cited by examiner

Primary Examiner—Robert H. Kim
Assistant Examiner—Pamela R. Hobden
(74) Attorney, Agent, or Firm—Fenster & Company Patent Attorneys Ltd.

(57) ABSTRACT

A method for reconstructuring a planar image slice in a CT scanner having a predetermined reconstrunction angle and including a detector array having n rows, n being an integer greater than 1, said method comprising: acquiring X-ray attentuation data from the detector array along a predetermined portion of a helical scan path in the vicinity of an axial position corresponding to the planar image slice, wherein the predetermined portion has an angular extent that is generally equal to the reconstruction angle; and processing the data to reconstruct an image of the slice, using data acquired substantially only along the predetermined portion of the scan path.

31 Claims, 3 Drawing Sheets

ON-LINE IMAGE RECONSTRUCTION IN HELICAL CT SCANNERS

RELATED APPLICATION

This application is a US National filin of PCT Application PCT/IL98/00075, filed Feb. 12, 1998.

FIELD OF THE INVENTION

The present invention relates generally to computerized tomographic (CT) imaging, and specifically to multi-slice CT scanners having helical scan paths.

BACKGROUND OF THE INVENTION

Helical-path CT scanners are well known in the art. Generally, such scanners comprise an X-ray tube, mounted on an annular gantry, so as to revolve continuously about a subject being imaged. The subject lies on a bed, which is translated continuously through the gantry simultaneously with the tube's revolution. An array of X-ray detectors on the opposite side of the subject from the X-ray tube receive radiation transmitted through the subject. The detectors generate signals proportional to the attenuated X-ray flux incident thereon. The signals are pre-processed to produce attenuation data, which are used in reconstructing orimages of the subject. In "third-generation" scanners, the array of detectors is mounted on the gantry so as to revolve along with the X-ray tube, whereas in "fourth-generation" scanners, the detectors are arrayed in a ring, which is generally stationary.

The axis of translation of the bed (conventionally the Z-axis) is generally parallel to the long axis of the subject's body, which is typically perpendicular to the plane of revolution of the tube. Thus, the path of the X-ray tube relative to the subject generally describes a helix about this axis, and X-ray attenuation data received from the X-ray detector array similarly correspond to a series of helically-disposed angular "views" through the subject.

In order to reconstruct a planar cross-sectional image slice of the subject at a desired axial position, based on the helical-scan views, effective attenuation values for each of a plurality of points around a circumference of such a planar slice are derived by interpolation between data received in the original helical-path views. For each of the plurality of points, the respective effective attenuation values thus correspond to the approximate attenuation along rays within the planar slice that pass through the point. For 360° reconstruction, as is known in the art, the plurality of points are distributed around the entire circumference of the slice. For 180° reconstruction, also known in the art, the points are distributed over an extent equal to half the circumference plus the "fan angle," i.e., the angular field of view covered by the fan-shaped X-ray beam. (For convenience in the following discussion, we will refer to the total angular extent of all the views that are collectively used in the reconstruction of a complete planar slice as the "reconstruction angle," typically 360° or 180°.) The interpolated effective attenuation values are filtered and back-projected to produce the cross-sectional image.

In general, to derive effective attenuation values for a given view angle and axial position, it is necessary to interpolate between actual data from at least two different views at that view angle, bracketing the axial position of the planar slice. The two views are acquired in successive scan segments, separated by the fall reconstruction angle. Because data from two different scan segments must typically be combined to reconstruct each planar image slice, data from the earlier of the two scans must be stored in buffer memory. Two full scans, comprising twice the total reconstruction angle, are thus needed to produce a single cross-sectional image. Reconstruction of each planar image slice lags behind acquisition of the data in the earlier of the two scans by at least the time it takes the tube to make a full scan around the subject. By comparison, in axial (non-helical) CT scanners, successive views may be processed in a "pipeline" data flow, so that the slice image is displayed with a minimal delay after completion of a single scan. The lag in helical scan reconstruction is particularly disadvantageous when CT imaging is used to track the progress of a physiological process, such as the flow of a contrast material.

Multi-slice helical-path scanners are known in the art. For example, U.S. Pat. No. 5,485,493, which is incorporated herein by reference, describes a multiple-detector-ring spiral scanner with relatively adjustable helical paths, in which two adjacent, parallel slices are acquired along two parallel paths simultaneously or sequentially. Data corresponding to planar slices are derived by interpolating between data acquired along the two helical paths.

U.S. Pat. No. 5,524,130, the disclosure of which is incorporated herein by reference describes a number of methods for utilizing a single detector ring scanner to provide successive axially spaced slices with reduced time between reconstruction of the slices. Some of these methods appear to utilize partial scan data from one scan to replace data from a second scan taken at a different time for reducing the reconstruction time.

SUMMARY OF THE INVENTION

It is an object of the present invention to provide a method for on-line image reconstruction of helical-scan CT data.

In one aspect of the present invention, the CT data comprise multiple-slice CT data, acquired using a multi-row detector array.

In preferred embodiments of the present invention, a multi-slice helical-scan CT scanner comprises an X-ray tube, mounted to revolve on an annular gantry about a bed on which a subject lies, and a detector array. The bed is advanced through the gantry along a translation axis that is generally parallel to the long axis of the subject's body. The X-ray tube thus describes a generally helical trajectory about the subject's body and irradiates the subject from multiple positions, or "views," along this trajectory. The detector array preferably comprises two or more parallel rows of X-ray detector elements, each row having a long axis disposed in a generally circumferential direction with respect to the long axis of the subject's body. The detector elements receive radiation that has passed through the subject's body at each of the views and generate signals responsive to attenuation of the X-rays.

Preferably, for 360° CT image reconstruction, the width of the detector array which is exposed to radiation, measured in a direction parallel to the translation axis, is substantially greater than the pitch of the helical trajectory. For 180° reconstruction, the width of the detector array which is exposed to radiation is substantially greater than half the pitch of the helical trajectory.

For each view, the two or more rows of the array simultaneously generate corresponding line attenuation signals. These signals are preprocessed, as is known in the art. The resultant line attenuation data are interpolated to generate geometrically-corrected effective attenuation values, which are associated with planar slices through the body that are generally perpendicular to the translation axis. The corrected effective attenuation values are filtered and back-projected to calculated CT values, which are used to update cross-sectional CT images substantially in real time.

In preferred embodiments of the present invention, an effective attenuation value is calculated for each of a plurality of points on a periphery of each planar slice by weighted interpolation between first and second measured attenuation values, taken from respective first and second line attenuation signals within a single, multiple-slice view. The values are preferably calculated by linear interpolation, but may alternatively be calculated using non-linear or other helix interpolation schemes known in the art. The first and second line attenuation signals are derived respectively from data received simultaneously from first and second rows of detector elements. Thus, there is no need for any additional buffer memory to store data from a preceding scan (although the data may be stored if desired), and a complete cross-sectional CT image may be acquired and immediately reconstructed within a time window corresponding to a single rotation of the tube over the reconstruction angle.

In some preferred embodiments of the present invention, a time sequence of images of a single planar slice at a selected axial position is reconstructed, as described above, using data acquired from a helical scan in a vicinity of the position. Each image in the sequence is reconstructed from data acquired during a different time "window." The successive images in the sequence are preferably processed and displayed on line, as described, for example, in Israel patent application number 120227 entitled "Real-time Dynamic Image Reconstruction," filed on Feb. 20, 1997 and a corresponding PCT patent application of the same title filed on the same day as the present application. The disclosure of both these applications incorporated herein by reference.

In some preferred embodiments of the present invention, a series of planar slices are reconstructed at a corresponding series of axial positions covering a range of interest within the subject's body. Data are acquired from a helical scan in a vicinity of a first position in the series. A first planar slice at the first position is then reconstructed and displayed, as described above, while data are acquired in a vicinity of a second, subsequent position in the series. This process of acquisition, reconstruction and display is preferably repeated with respect to a third position, fourth position, and so forth, over the entire series.

In these preferred embodiments, the data acquired in the vicinity of each of the positions is preferably stored and used in subsequent image processing, reconstruction and display. Thus, for example, at least some of the data acquired in the vicinity of the first slice may be incorporated in the reconstruction of the second slice, and so forth. By using such overlapping data sets in reconstructing image slices at successive positions, closely-spaced slices may be produced, so that features within the subject's body may be seen in greater detail. Additionally, the CT scanner may be adapted to reconstruct two or more such slices simultaneously, so that multiple slices may be reconstructed and displayed in rapid succession.

It will be appreciated that the principles of the present invention are equally applicable to third- and fourth-generation CT scanners and to various image reconstruction methods, including 180°, 360°, fan beam and parallel beam reconstruction, as are known in the art. Moreover, although in the preferred embodiments described herein, the Z-axis, along which the bed advances, is generally perpendicular to the plane of revolution of the tube, the principles of the present invention may similarly be applied to CT image reconstruction using angled helical scan paths, as described in a PCT patent application PCT/IL97/00069, filed on Feb. 20, 1997, entitled "Helical Scanner with Variably Oriented Scan Axis," which is assigned to the assignee of the present invention, and whose disclosure is incorporated herein by reference. This application designates the US.

It will be appreciated that, 180 degree and 360 degree rotations are utilized in the above description for simplicity. However, actual data collection may extend to the reconstruction angle plus the fan beam angle under certain reconstruction schemes. Such a reconstruction angle is included within the meaning of the term "generally equal to the reconstruction angle" as that term is used herein.

There is thus provided, in accordance with a preferred embodiment of the invention, a method for reconstructing a planar image slice in a CT scanner having a predetermined reconstruction angle and including a detector array having n rows, n being an integer greater than 1, said method comprising:

acquiring X-ray attenuation data from the detector array along a predetermined portion of a helical scan path in a vicinity of an axial position corresponding to the planar image slice, wherein the predetermined portion has an angular extent that is generally equal to the reconstruction angle; and processing the data to reconstruct an image of the slice, using data acquired substantially only along the predetermined portion of the scan path.

Preferably, acquiring X-ray data from the detector array comprises acquiring data from detector elements in at least two rows of the detector array, and processing the data comprises interpolating the data acquired from the at least two rows.

Preferably, acquiring X-ray attenuation data along the predetermined portion of the helical scan path comprises acquiring data along a helical path having a pitch that is less than or equal to (n−1)/n times a width of the detector array, measured in the axial direction, and wherein processing the data to reconstruct the image comprises processing the data using 360° reconstruction.

Alternatively, acquiring X-ray attenuation data along the predetermined portion of the helical scan path comprises acquiring data along a helical path having a pitch that is less than or equal to 2(n−1)/n times a width of the detector array, measured in the axial direction, and wherein processing the data to reconstruct the image comprises processing the data using 180° reconstruction.

Preferably, processing the data to reconstruct the image comprises processing the data for a given portion while the data is being acquired.

A preferred embodiment of the method comprises acquiring data along a second, successive portion of the scan path, wherein processing the data to reconstruct the image comprises processing the data acquired along the predetermined portion of the helical scan path while acquiring the data along the second portion. Preferably, processing the data acquired along the predetermined portion of the helical scan path comprises displaying the image while acquiring data along the second portion. Preferably, the method includes processing the data acquired along the second portion of the scan path to reconstruct a second image. Preferably, the method further includes storing at least some of the data acquired along the predetermined portion of the scan path, wherein processing the data acquired along the second portion of the scan path comprises processing the data acquired along the second portion together with the stored data acquired along the predetermined portion to reconstruct the second image.

In a preferred embodiment of the invention, processing the data acquired along the second portion of the scan path to reconstruct the second image comprises deriving CT values from the data and averaging the values with other CT values derived from the attenuation data acquired along the predetermined portion of the scan path.

In a preferred embodiment of the invention, processing the data acquired along the second portion of the scan path to reconstruct the second image comprises deriving CT values from the data and subtracting the values from other CT values derived from the attenuation data acquired along the predetermined portion of the scan path.

Preferably, processing the data acquired along the second portion of the scan path to reconstruct the second image comprises producing an image of the slice having improved image quality. Preferably, processing the data acquired along the second portion of the scan path to reconstruct the second image comprises producing an image showing a change in the body of a subject in a vicinity of the slice.

In a preferred embodiment of the invention, processing the data comprises displaying the image and the second image in a cine mode.

There is furter provided, in accordance with a preferred embodiment of the invention, a method for reconstructing a planar image slice in a helical mode CT scanner having a predetermined reconstruction angle and including a detector array having a plurality of rows detectors, the method comprising:

reconstructing said slice using data acquired during a first time window to form a first image; and reconstructing said slice using data acquired during a later time window to form a second image.

Preferably, the method includes successively displaying said first and second images.

In a preferred embodiment of the invention, wherein the first and second images are reconstructed using data acquired by more than one row of detectors and wherein at least one of the rows used to reconstruct one of the images is different from any of the rows used to reconstruct the other of the images.

In a preferred embodiment of the invention, the method includes reconstructing and displaying a third image of the slice from data acquired during a third time window.

The present invention will be more fully understood from the following detailed description of the preferred embodiments thereof, taken together with the drawings in which:

DETAILED DESCRIPTION OF PREFERRED EMBODIMENTS

Figure 1:
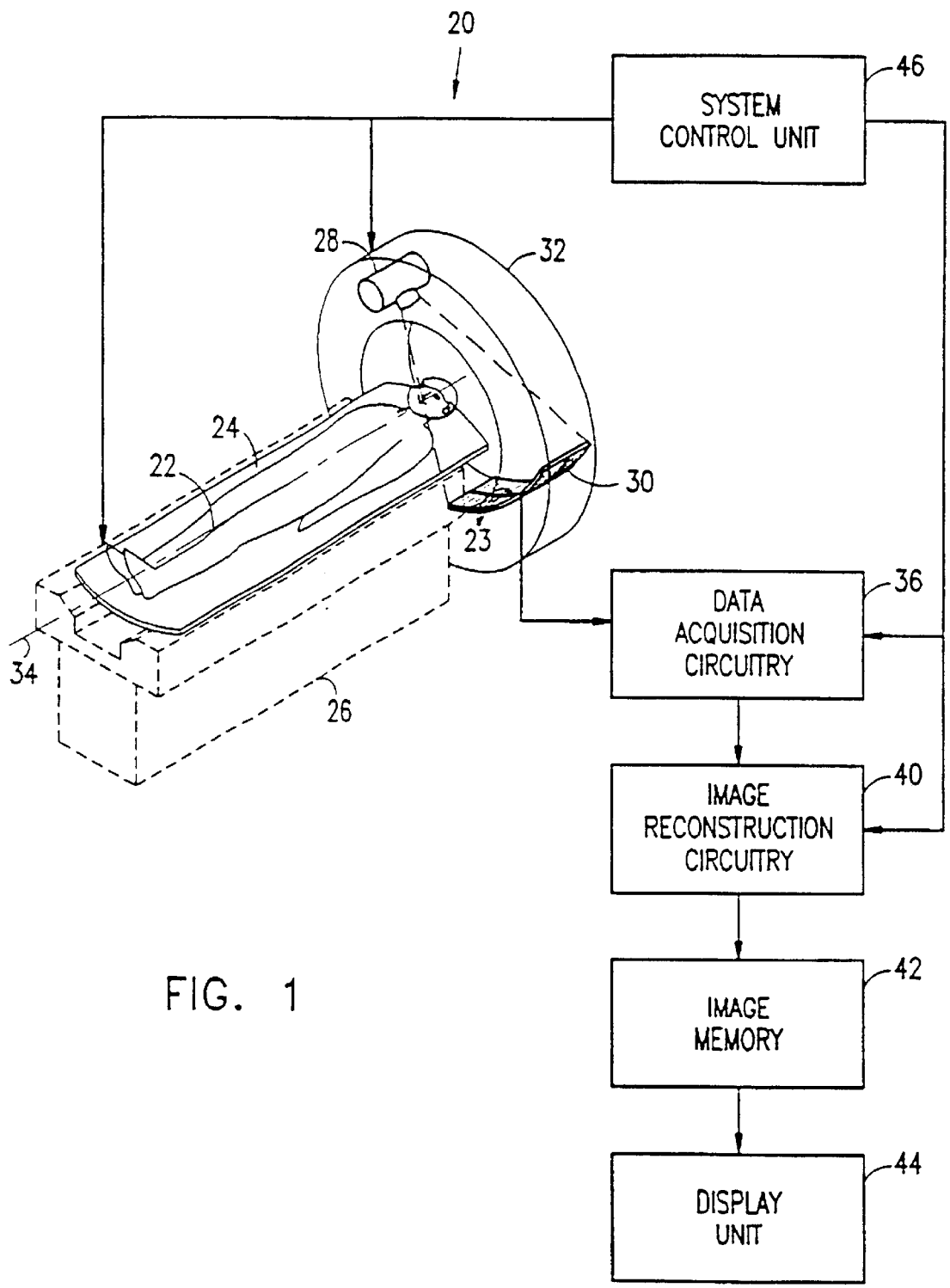
FIG. 1 is a schematic illustration of a multi-slice helical-scan CT scanner, operative in accordance with a preferred embodiment of the present invention.

Reference is now made to FIG. 1, which shows schematically a CT scanner 20, operative in accordance with a preferred embodiment of the present invention. Scanner 20 comprises a bed 24, supported by a base 26, on which bed a subject 22 lies while his body is being imaged by the scanner. Scanner 20 further comprises an X-ray tube 28, which irradiates subject 22, and a detector array 30, which receives X-rays from tube 28 and generates signals responsive to the attenuation of the X-rays in passing through the subject's body. Preferably, array 30 comprises multiple, parallel rows of X-ray detector elements 23. Tube 28 and array 30 are mounted on an annular gantry 32, so as to revolve about subject 22. Simultaneously, bed 24 is advanced through gantry 32 along an axis 34, taken to be the Z-axis of a scanning coordinate system. Z-axis 34 is generally parallel to the long axis of the subject's body.

Scanner 20 as pictured in FIG. 1 is of a type known in the art as a third-generation CT-scanner, characterized in that both tube 28 and detector array 30 revolve about subject 22. It will be appreciated, however, that the principles of the present invention and the methods of image reconstruction to be described below are equally applicable to other types of CT scanners, in particular fourth-generation CT scanners, in which the detectors form a substantially stationary ring around subject 22.

As tube 28 revolves and bed 24 advances, the tube describes a generally helical path around axis 34. Preferably, bed 24 moves with substantially constant velocity, so that the helical path has a constant pitch. At each of a plurality of selected locations of tube 28, generally uniformly spaced along this path, data acquisition circuitry 36 acquires a "view," i.e., the circuitry receives signals from each element 23 of array 30 responsive to X-ray attenuation along a ray from tube 28 to the element. Each such view comprises a plurality of parallel line attenuation signals, each such line signal corresponding to one of the multiple rows of array 30.

For each view, data acquisition circuitry 36 performs signal normalization and logarithm operations, as are known in the art, to derive X-ray attenuation data corresponding to each of elements 23. Image reconstruction circuitry 40 receives these data and performs interpolation operations to derive effective attenuation values at a plurality of points on a periphery of a planar image slice, at a selected position along Z-axis 34. For each of the plurality of points, each such effective attenuation value corresponds to the attenuation along a ray in the slice that passes through the point. These effective values are filtered and back5 projected, using methods known in the art, to produce a corrected, planar image slice at the selected position. A plurality of these planar image slices are typically produced, so as to reconstruct a three-dimensional CT image set of the body of subject 22. Preferably, these image slices are stored in image memory 42 and displayed by display unit 44, and they may be otherwise printed and/or processed as is known in the art.

Figure 2:
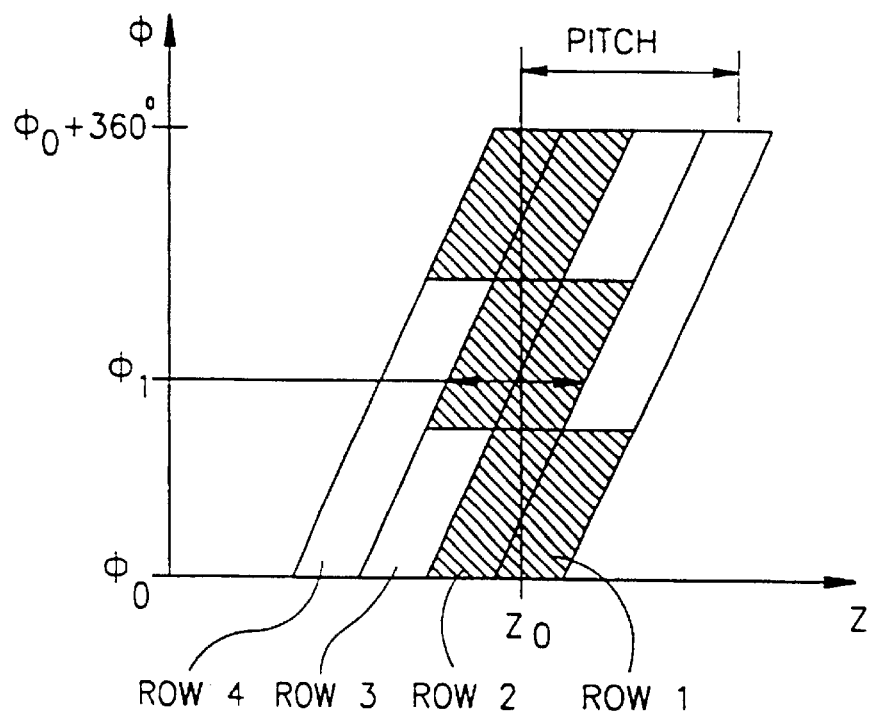
FIG. 2 is a graph that schematically illustrates an aspect of the operation of the scanner of FIG. 1, in accordance with a preferred embodiment of the present invention.

FIG. 2 illustrates the operation of CT scanner 20, in accordance with a preferred embodiment of the present invention. Array 30 is taken to comprise four parallel, adjoining rows of detectors 23, from which signals are received simultaneously at each view angle θ. FIG. 2 shows the respective detection areas of the four rows (along the Z-dimension), labeled as ROW 1 through ROW 4, over 360° of rotation of gantry 32. As described above, the rows of array 30 advance along the Z-axis simultaneously with the revolution of tube 28, so that the view angle θ increases linearly with Z from $\theta_o$ to $\theta_o+360°$ in each turn of the above-mentioned helical path described by the tube.

As shown by FIG. 2, the helical path preferably has a pitch equal to ¾ of the total width of array 30 in the Z-direction. Other values of pitch can also be used, and the principles of the present invention, as will be described below, can equally be applied to CT scanners that include detector arrays having two, three or more rows. Preferably, for 360° reconstruction and two-point interpolation of the attenuation values, the pitch of the helical path is equal to or less than $(n-1)/n$, where n is the number of rows of the detector array. Under these conditions, an image can be reconstructed, as described below, from data acquired over a single 360° revolution of gantry 32.

To reconstruct a planar image slice at position $Z_o$, attenuation data are acquired from a plurality of views within a single revolution of tube 28, beginning and ending at a revolution angle $\theta_o$, as shown in FIG. 2. For each value of $\theta$ around the periphery of the slice at $Z_o$, an effective attenuation value is determined by interpolating between measured attenuation data, acquired in a single view from two rows of array 30. Thus, for example, an effective attenuation value corresponding to a view angle $\theta_1$ in the planar slice at $Z_o$ will be found by appropriately interpolating between measured data from rows 2 and 3 at this view angle. In this manner, the entire planar slice at $Z_o$ (or any other Z-axis position) is reconstructed from attenuation data acquired during a single revolution along the helical path of tube 28.

It is thus possible, if desired, to reconstruct the image in real time while the gantry revolves about the patient and data is acquired. The image will be displayed on display unit 44 very shortly after the rotation is completed.

If the pitch of the helical path of tube 28 is substantially less than $(n-1)/n$ times the width of array 30, for example, if the pitch is equal to half the width, then in accordance with the principles of the present invention, effective attenuation values may also be interpolated between measured data from more than two rows at each view angle within a single revolution of the tube. Widening the range of interpolation in this manner may be useful in reducing image artifacts.

The preferred embodiment described here with reference to FIG. 2 assumes that CT scanner 20 uses 360° reconstruction to produce the planar image slices. It will be appreciated here and in reference to other preferred embodiments of the present invention to be described below, that substantially similar preferred embodiments of the present invention are also possible using 180° reconstruction. In 180° reconstruction, planar image slices are reconstructed using data from a half-revolution only, with views covering 180° or slightly more, as is known in the art. The 180° technique gives faster reconstruction, at the expense of reduced resolution and contrast and/or increased image artifacts. In the descriptions herein of preferred embodiments of the present invention, unless indicated otherwise, it will be understood that the techniques described with reference to 360° reconstruction are also applicable to 180° reconstruction, and vice versa, with scan angles adjusted appropriately when required.

Figure 3:
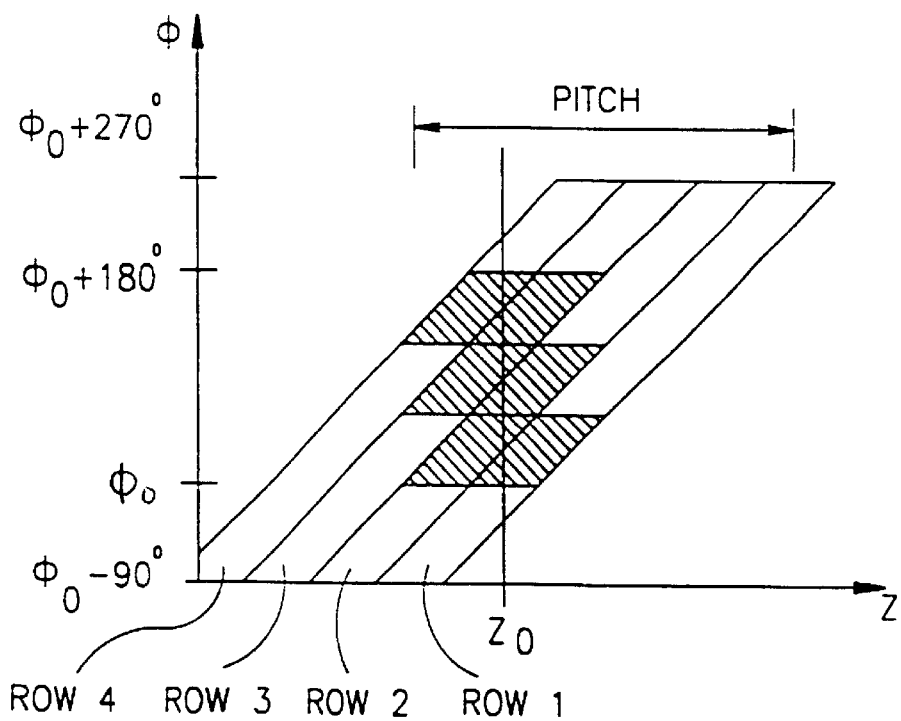
FIG. 3 is a graph that schematically illustrates the aspect of the operation of the scanner that is illustrated by FIG. 2, in accordance with an alternative preferred embodiment of the present invention.

Thus, FIG. 3 schematically illustrates, in a manner similar to FIG. 2, the operation of CT scanner 20 using 180° reconstruction, in accordance with another preferred embodiment of the present invention. An image slice at $Z_o$ is reconstructed using data acquired from the four rows of array 30 over a half-revolution of gantry 32, from $\theta_o$ to $\theta_o+180°$. The use of 180° reconstruction allows the helical path of tube 28 to have a substantially greater pitch than in 360° reconstruction. In the case shown in FIG. 3, the pitch is equal to 1.5 times the width of detector array 30. For 180° reconstruction in accordance with the principles of the present invention, using a detector array having n rows, the pitch is preferably equal to or less than $2(n-1)/n$ times the width of the array.

As described above, 180° reconstruction typically uses data acquired over an angular extent that is somewhat greater than 180°, generally by an amount equal to the fan angle of the X-ray beam. For the sake of simplicity in describing the present invention, this difference will be disregarded. It will be clear to those skilled in the art how the methods described herein may be adapted to take the fan angle into account.

Figure 4:
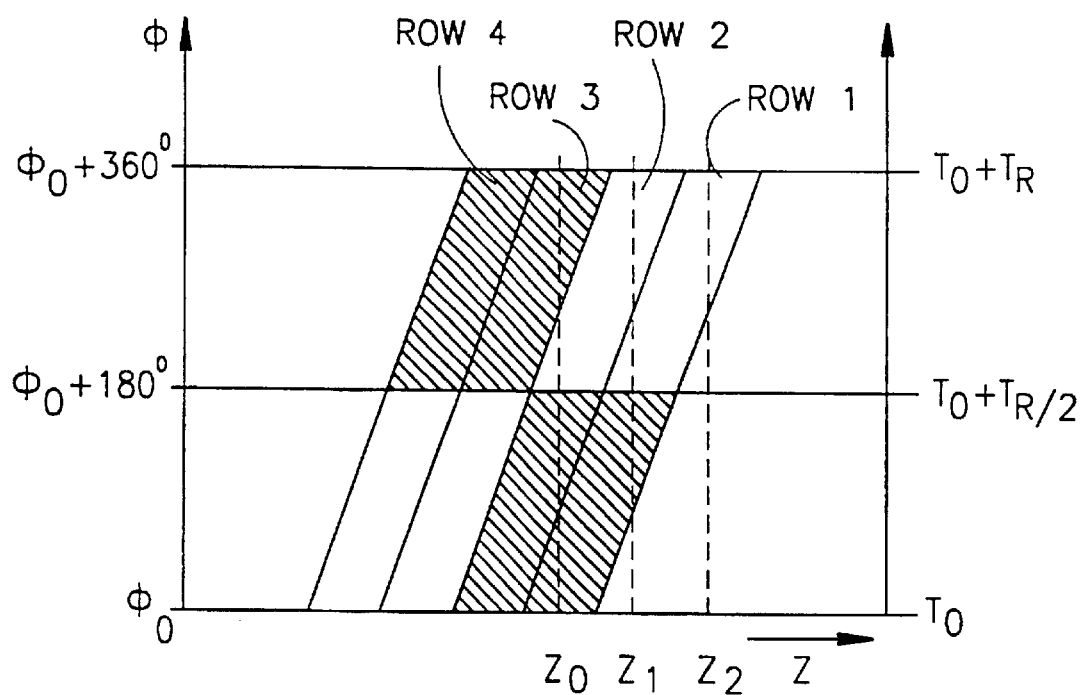
FIG. 4 is a graph that schematically illustrates another aspect of the operation of the scanner of FIG. 1, in accordance with a preferred embodiment of the present invention.

FIG. 4 schematically illustrates the Z-dimension of the detection area covered by each of the rows of array 30, over a 360° revolution of gantry 32, in accordance with another preferred embodiment of the present invention. The vertical axis at the left of the graph shows the view angle $\theta$, as described above. The vertical axis at the right of the graph shows the average time at which the successive views are acquired, wherein the scan begins at a time $T_o$, and $T_R$ is the time required for a complete revolution of gantry 32. It should be understood, that due to fan beam to parallel beam rebining, each view is actually acquired during a short time window and not at a specific time. The helical scan path represented by FIG. 4 has a pitch equal to half the width of the array.

As shown in FIG. 4, assuming that 180° reconstruction is used, an image corresponding to axial position $Z_o$ may be reconstructed using data acquired from ROW 1 and ROW 2 over a time "window" from $T_o$ to $T_o+T_R/2$. A second image may similarly be reconstructed at $Z_o$ using data acquired from ROW 2 and ROW 3 over the time window from $T_o+T_R/2$ to $T_o+T_R$. Another such image may subsequently be reconstructed from ROW 3 and ROW 4, and similarly, an image at $Z_o$ may be reconstructed from data acquired over any half-revolution within the time interval from $T_o$ to $T_o+3T_R/2$. Each of the images reconstructed in this manner represents substantially the same cross-sectional slice through subject 22, seen in a different, respective time window.

Preferably, the images corresponding to successive time windows are reconstructed in pipeline manner, during the scan, and are displayed on-line by display unit 44. More preferably, the images are displayed successively a quasi-continuous, "cine" mode, and thus show changes occurring in the body of subject 22 at the slice position $Z_o$.

Alternatively or additionally, images at $Z_o$ having overlapping time windows may be reconstructed and displayed in this manner. In this case, to reduce computational effort, the entire image is preferably not reconstructed for each time window. Rather, for each successive, overlapping window, a partial matrix of new CT values is calculated and added into the image, while a corresponding matrix from the first half of the window is subtracted. Alternatively, the new matrix may be averaged with the corresponding matrix from the preceding window, so as to modify and/or improve the quality of the image. Methods of modifying and updating the image are further described in the above-mentioned PCT patent application entitled "Real-time Dynamic Image Reconstruction," incorporated herein by reference.

For 360° reconstruction, image slices may similarly be acquired and updated, as long as the pitch of the helical path of tube 28 is substantially less than $(n-1)/n$ times the width of array 30.

Preferably, a series of planar slices are reconstructed at a corresponding series of axial positions covering a range of interest within the body of subject 22. $Z_o$ may, for example, be the first position in such a series, followed by subsequent positions $Z_1$, $Z_2$, etc., along the Z-axis, as shown in FIG. 4. Image reconstruction circuitry 40 receives data over an angular range substantially equal to the reconstruction angle and reconstructs a first planar image slice at $Z_o$, as described above. While the slice at $Z_o$ is being reconstructed, data are acquired over a similar angular range in the vicinity of $Z_1$. Preferably, the image slice at $Z_o$ is displayed by display unit 44 while the slice at $Z_1$ is reconstructed. This process of acquisition, reconstruction and display is preferably repeated with respect to $Z_2$, and so forth, over the entire series.

Further preferably, the data acquired in the vicinity of each of the positions $Z_o$, $Z_1$, $Z_2$, etc., is stored and used in subsequent image processing, reconstruction and display. Thus, for example, at least some of the data used in reconstructing the slice at $Z_o$ are incorporated in the reconstruction of the slice at Z1, and so forth. By using such overlapping data sets in reconstructing image slices at successive positions, closely-spaced slices may be produced, so that features within the subject's body may be seen in greater detail. Additionally, image reconstruction circuitry 40 is preferably adapted to reconstruct two or more such slices simultaneously, so that multiple slices may be reconstructed and displayed in rapid succession.

It will be apparent to those skilled in the art that the principles of the present invention may be applied to CT scanners of various types, including multi-slice scanners that simultaneously produce multiple planar image slices, and oblique scanners, which produce image slices along planes at oblique angles relative to the long axis of the subject's body.

It will be appreciated that, 180 degree and 360 degree rotations are utilized in the above description for simplicity. However, actual data collection may extend to the reconstruction angle plus the fan beam angle under certain reconstruction schemes. Such a reconstruction angle is included within the meaning of the term "generally equal to the reconstruction angle" as that term is used herein.

It will farther be appreciated that the preferred embodiments described above are cited by way of example, and the full scope of the invention is limited only by the claims.

What is claimed is:

1. A method for reconstructing a planar image slice in a CT scanner at a given axial position having a predetermined reconstruction angle and including a detector array having n rows, n being an integer greater than 1, said method comprising:

acquiring X-ray attenuation data from the detector array along a predetermined portion of a helical scan path in a vicinity of the axial position corresponding to the planar image slice, wherein the predetermined portion has an angular extent that is generally equal to the reconstruction angle;

processing the data to reconstruct an image of the slice, using data acquired substantially only along the predeternined portion of the scan path, acquiring data alone a second. successive portion of the helical scan path; and processing the data acquired along the second portion of the scan path to reconstruct a second image of the slice, said second image showing a change in the body of a subject at the axial position.

2. A method according to claim 1, wherein acquiring X-ray data from the detector array comprises acquiring data from detector elements in at least two rows of the detector array, and processing the data comprises interpolating the data acquired from the at least two rows.

3. A method according to claim 1, wherein acquiring X-ray attenuation data along the predetermined portion of the helical scan path comprises acquiring data along a helical path having a pitch that is less than or equal to (n−1)/n times a width of the detector array, measured in the axial direction, and wherein processing the data to reconstruct the image comprises processing the data using 360° reconstruction.

4. A method according to claim 1, wherein acquiring X-ray attenuation data along the predetermined portion of the helical scan path comprises acquiring data along a helical path havin, a pitch that is less than or equal to 2(n−1)/n times a width of the detector array, measured in the axial direction, and wherein processing the data to reconstruct the image comprises processing the data using 180° reconstruction.

5. A method according to claim 1 wherein processing the data to reconstuct the image comprises processing the data for a given portion of the helical scan while the data is being acquired.

6. A method according to claim 1 wherein processing the data to reconstruct the image comprises processing the data acquired along the predetermined portion of the helical scan path while acquiring the data along the second portion of the helical scan path.

7. A method according to claim 6, wherein processing the data acquired along the predeteminued portion of the helical scan path comprises displaying the image while acquiring data along the second portion.

8. A method according to claim 1, and comprising storing at least some of the data acquired along the predetermined portion of the scan path, wherein processing the data acquired along the second portion of the scan path comprises processing the data acquired along the second portion together with the stored data acquired along the predetermined portion to reconstruct the second image.

9. A method according to claim 1, wherein processing the data acquired along the second portion of the scan path to reconstruct the second image comprises deriving CT values from the data and averaging the values with other CT values derived from the attenuation data acquired along the predeternined portion of the scan path.

10. A method according to claim 1, wherein processing the data acquired along the second portion of the scan path to reconstruct the second image comprises deriving CT values from the data and subtracting the values from other CT values derived from the attenuation data acquired along the predetermined portion of the scan path.

11. A method according to claim 1, wherein processing the data acquired along the second portion of the scan path to reconstmct the second image comprises producing an image of the slice having improved image quality.

12. A method according to claim 1, wherein processing the data comprises displaying the image and the second image in a cine mode.

13. A method for reconstructing a planar image slice in a helical mode CT scanner having a predetermined reconstruction angle and including a detector array having a plurality of rows detectors, the method comprising:

reconstructing said slice using data acquired during a first time window to form a first image; and reconstructing said slice using data acquired during a later time window to form a second image.

14. A method according to claim 13 and including:

successively displaying said first and second images.

15. A method according to claim 13 wherein the first and second images are reconstructed using data acquired by more than one row of detectors and wherein at least one of the rows used to reconstruct one of the images is different from any of the rows used to reconsuct the other of the images.

16. A method according to claim 13, and comprising reconstructing and displaying a third image of the slice from data acquired during third time window.

17. A CT scanner comprising:
- a detector array having n rows of detector elements, n being an integer greater than 1, capable of acquiring X-ray attenuation data along a predetermined portion of a helical scan path in a vicinity of an axial position corresponding to a planar image slice to be reconstructed, wherein the predetermined portion has an angular extent that is generally equal to a predetermined reconstruction angle; and
- a processor capable of processing the data to reconruct an image of the slice, using data acquire substantially only along the predetermined portion of the scan path and processing the data acquired along a second portion of the scan path to reconstruct a second image of the slice, said second image showing a change in the body of a subject at the axial position.

18. Apparatus according to claim 17, wherein the processor is capable of X-ray data from at least two rows of the detector array, and interpolates the data acquired from the at least two rows in reconstructing the slices.

19. Apparatus according to claim 17, wherein the processor is capable of processing X-ray attenuation data acquired along a helical path having a pitch that is less than or equal to $(n-1)/n$ times a width of the detector array, measured in the axial direction, and processes the data to reconstruct the image using 360° reconstruction.

20. Apparatus according to claim 17, wherein the processor is capable of processing X-ray attenuation data acquired along a helical path having a pitch that is less than or equal to $2(n-1)/n$ times a width of the detector array, measured in the axial direction, and processes the data to reconstrct the image using 180° reconstruction.

21. Apparatus according to claim 17 wherein the processor is capable of processing the data for a given portion of the helical scan while the data is being acquired.

22. Apparatus according to claim 17, wherein the processor is capable of processing the data acquired along the predetermined portion of the helical scan path while acquiring the data along the second portion of the helical scan path.

23. Apparatus according to claim 22, including a display wherein the processor is capable of displaying the image on the display while data is acquired along the second portion.

24. Apparatus according to claim 17, and comprising a memory capable of storing at least some of the data acquired along the predetermined portion of the scan path, wherein the processor is capable of processing the data acquired along the second portion together with the stored data acquired along the predetermnned portion to reconstruct the second image.

25. Apparatus according to claim 17, wherein the processor is capable of deriving CT values from the data and averaging the values with other CT values derived fom the attenuation data acquired along the predetermined portion of the scan path.

26. Apparatus according to claim 17, wherein the processor is capable of deriving CT values from the data and subtracting the values from other CT values derived from the attenuation data acquired along the predetermined portion of the scan path.

27. Apparatus according to claim 17, including a display and wherein the processor is capable of displaying the image and the second image in a cine mode on the display.

28. Apparatus for reconstructing a planar image slice in a helical mode CT scanner having a predetermined reconstruction angle including:
- a detector array having a plurality of rows of detectors; and a processor capable of reconstructing said slice using data acquired during a first time window to form a first image and reconstructing said slice using data acquired during a later time window to form a second image.

29. Apparatus according to claim 28 and including:
- a display, wherein the processor is capable of successively displaying said first and second images.

30. Apparatus according to claim 28 wherein processor is capable of reconstructing the first and second images using data acquired by more than one row of detectors and wherein at least one of the rows used to reconstruct one of the images is different from any of the rows used to reconstruct the other of the images.

31. Apparatus according to claim 28, wherein the processor is capable of reconstructing and displaying a third image of the slice from data acquired during a third time window.

* * * * *